United States Patent [19]

Moorehead

[11] 4,177,809
[45] Dec. 11, 1979

[54] INTRAVENOUS CATHETER APPARATUS AND METHOD

[75] Inventor: Harvey R. Moorehead, Salt Lake City, Utah

[73] Assignee: Warner-Lambert Company, Morris Plains, N.J.

[21] Appl. No.: 833,628

[22] Filed: Sep. 15, 1977

[51] Int. Cl.² .............................................. A61M 5/00
[52] U.S. Cl. .......................... 128/214.4; 128/DIG. 16
[58] Field of Search ...................... 128/214.4, 221, 348, 128/DIG. 16

[56] References Cited

U.S. PATENT DOCUMENTS

| 3,399,674 | 9/1968 | Pannier et al. | 128/214.4 |
| 3,537,451 | 10/1970 | Beck et al. | 128/214.4 |
| 3,589,361 | 6/1971 | Loper et al. | 128/214.4 |
| 3,592,192 | 7/1971 | Harautuneian | 128/214.4 |
| 3,595,230 | 7/1971 | Suyeoka | 128/214.4 |
| 3,769,975 | 11/1973 | Nimoy et al. | 128/214.4 |
| 3,782,381 | 1/1974 | Winnie | 128/214.4 |
| 3,856,010 | 12/1974 | Moorehead et al. | 128/214.4 |
| 3,875,938 | 4/1975 | Mellor | 128/214.4 |
| 4,046,144 | 9/1977 | McFarlane | 128/214.4 |

FOREIGN PATENT DOCUMENTS

| 67214 | 6/1969 | German Democratic Rep. | 128/214.4 |
| 2258764 | 8/1975 | France | 128/214 R |
| 1459741 | 12/1976 | United Kingdom | 128/214.4 |

Primary Examiner—Dalton L. Truluck
Attorney, Agent, or Firm—David B. Ehrlinger; Frank S. Chow; Stephen Raines

[57] ABSTRACT

An intravenous catheter apparatus comprising an intravenous catheter tube, a manually guidable circumferentially deformable elastomeric bore-defining tubular inserter integral with and in axial alignment with the catheter tube for use with a patient, and a needle concentric within the catheter tube and inserter and extending through at least part of the bore of the inserter to beyond the distal end of the catheter tube, the inserter comprising opposed laterally extending wings adapted to be manually compressed together from an at-rest position to a needle control position, the bore of the inserter being sufficiently large to permit retraction of the needle from the catheter tube and the inserter when the inserter is at rest, and when the inserter wings are compressed to the needle control position being sufficiently constricted to enable the inserter to grip the needle firmly to permit inserter-forced injection of the distal end of the needle into the body of a patient.

13 Claims, 6 Drawing Figures

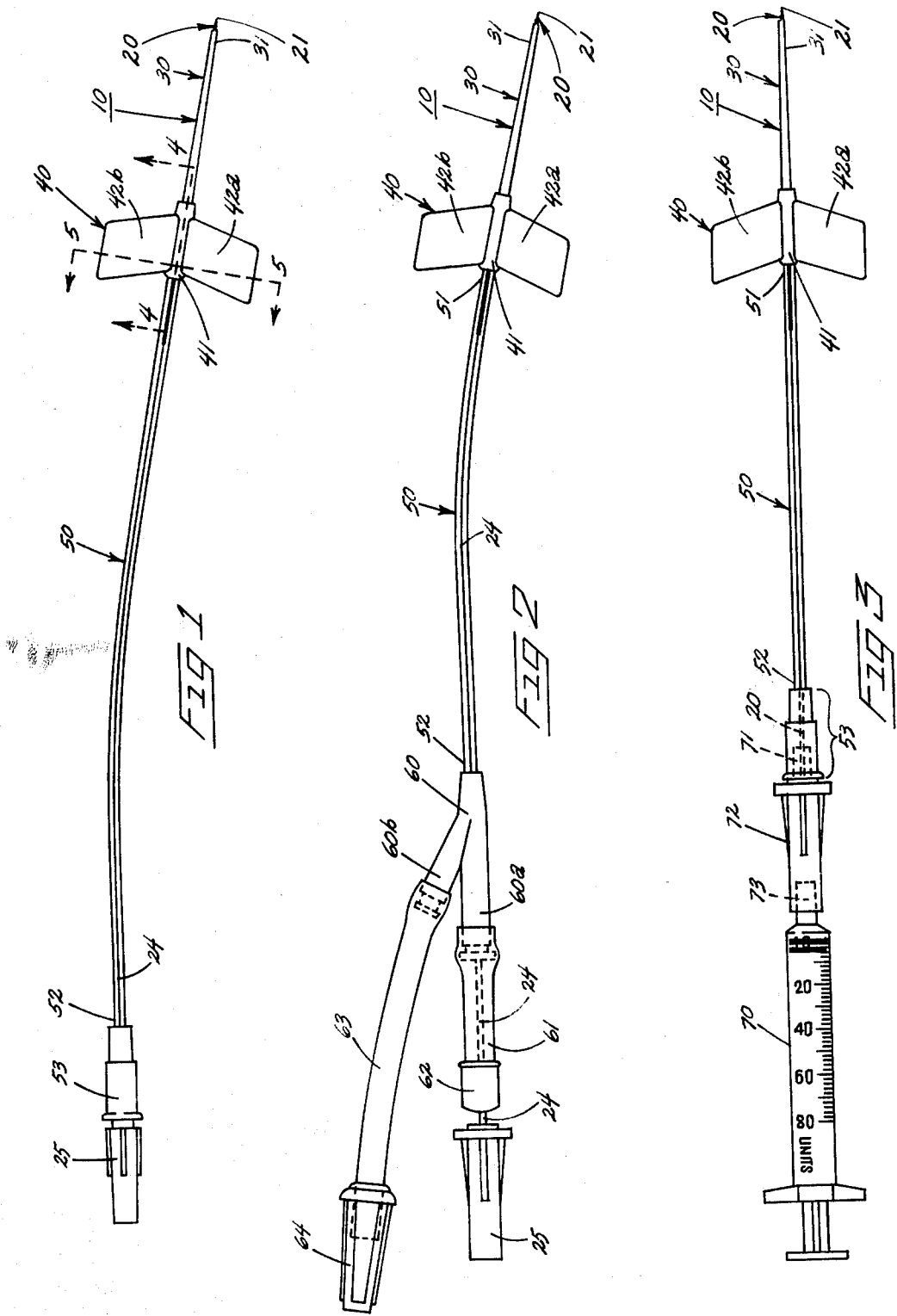

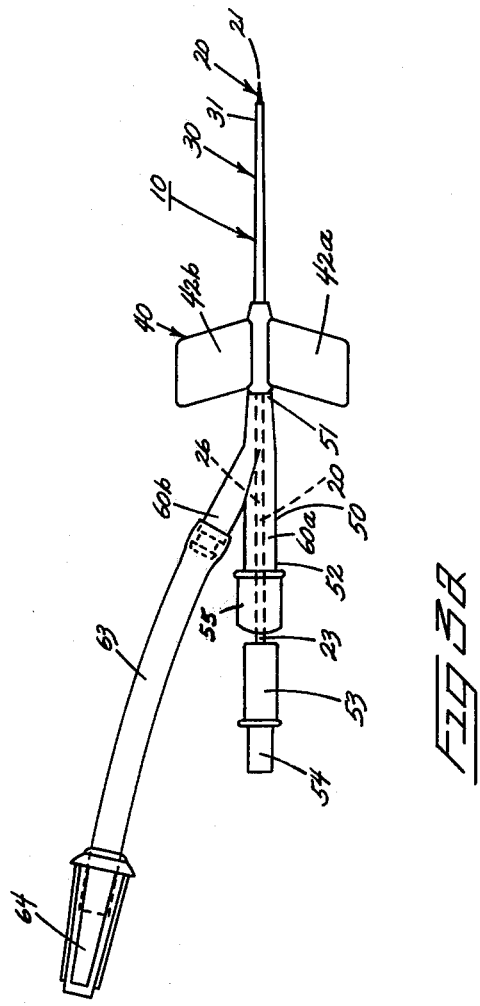

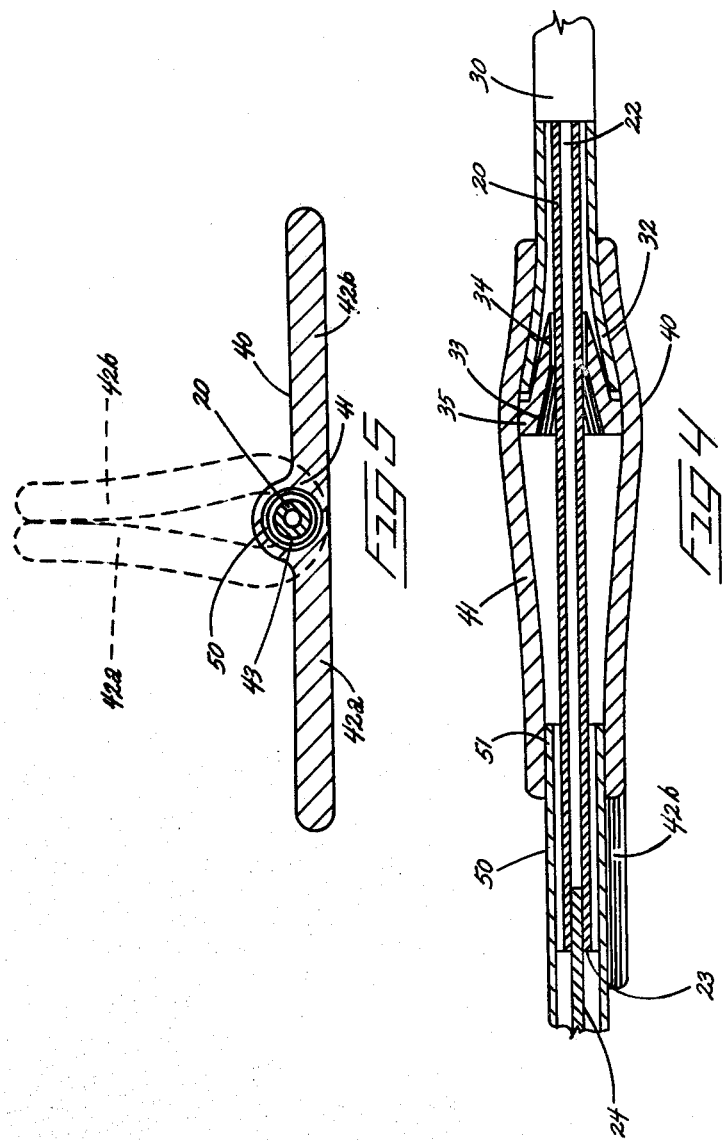

INTRAVENOUS CATHETER APPARATUS AND METHOD

SUMMARY AND DETAILED DESCRIPTION

This invention pertains generally to surgical methods and apparatus for removing fluids from patients or infusing fluids into patients and more specifically to methods and apparatus for carefully and accurately controlling the precise placement of a catheter tube within the body of a patient to accommodate fluid flow into or out of the body or to sample fluid flow rates and/or fluid pressures within the body.

It is well known and common practice by physicians to inject fluids and drugs directly into the blood stream of patients. Also, during surgical operations, it is frequently necessary to administer whole blood transfusions and parenteral fluids. Historically, introduction of such fluids into the cardiovascular system of a patient has required the making of a venipuncture using a hollow rigid needle having a proximal attachment site for fluid connecting the needed to a source of intravenous fluid or the like. This method of administering fluids created some persisting problems in the art. Primarily, the rigidity of the needle within the vein requires that the needle, usually on the arm, be maintained, for reasons of safety, in a fixed position at the general site of the venipuncture throughout the duration of fluid administration or transfusion, which may consume considerable time. Secondly, where it has been necessary to periodically draw blood samples and/or successively administer intravenous fluids, the patients may be required to experience a venipuncture each time, which repeated venipunctures are generally highly traumatic.

More recently it has been the practice to insert a flexible catheter tube into a vein and leave the catheter tube in such a position for purposes such as periodically administering fluids, transfusions and medication, collecting of blood samples, etc. In this way, the trauma, extravasation, infiltration, etc., of repeated venipunctures are avoided and the danger and discomfort of leaving a rigid needle in the body for a prolonged period of time are overcome. To place the distal end of such a flexible catheter tube within a body cavity, such as a vascular cavity, a cannulated or hollow needle is used to make the venipuncture. Thereafter, the catheter tube, telescopically carried on the outer circumference of the needle, is fed overtop of the needle into the vein following the venipuncture. The needle may thereafter be completely removed from the catheter tube and disposed of. For removal of the needle, it has been the practice to use a syringe hub-mounted needle or a retractable stylet needle assembly comprising a leading needle, a flexible wire rigidly secured to the trailing end of the needle, and a handle joined to the trailing end of the wire. Thus, the needle can be retracted from the catheter tube by means of the syringe or the retraction handle. However, according to practice, a catheter unit with a syringe needle or a retractable stylet needle must have an inserter clamp device which is structurally separate from and slideably engageable with the catheter tube for purposes of locking the needle at venipuncture and/or subsequent catheter placement. The inserter clamp device used, however, is relatively expensive to fabricate and must meet exacting dimensional specifications.

In view of the foregoing, it would be a significant contribution to the catheter art and is an object of the present invention to provide an intravenous catheter placement unit having a built-in inserter serving to facilitate controlled aseptic insertion and precise body placement of the catheter, which inserter is easily fabricated and is an integral part of the catheter.

The intravenous catheter apparatus of the present invention comprises an intravenous catheter tube, a manually guidable circumferentially deformable elastomeric bore-defining tubular inserter integral with and in axial alignment with the catheter tube for use with a patient, and a needle concentric within the catheter tube and the inserter and extending through at least part of the bore of the inserter to beyond the distal end of the catheter tube, the inserter comprising opposed laterally extending wings adapted to be manually compressed together from an at-rest position to a needle control position, the bore of the inserter being sufficiently large to permit retraction of the needle from the catheter tube and the inserter when the inserter is at rest, and when the inserter wings are compressed to the needle control position sufficiently constricted to enable the inserter to grip the needle firmly to permit inserter-forced injection of the distal end of the needle into the body of a patient.

In one preferred embodiment, the apparatus comprises a hollow needle which has an exposed beveled point to facilitate easy insertion into the body of a patient. Fixed to the proximal portion of the needle, is a narrow-gauge, flexible wire or the like which extends axially to the proximal end of the catheter unit where the wire integrally joins closure means for fluid control such as a male plug. The needle is sheathed in part by a catheter tube, preferably having a tapered distal end which is spaced immediately behind the exposed, beveled point of the needle. An inserter, integral with the trailing proximal end of the catheter, comprising a trailing tubular member, preferably as a separate piece and preferably a length of clear tubing, telescopically circumscribes the remainder of the needle and the stylet wire. The trailing tubular member terminates preferably in an enlarged female socket adapted to snugly receive a stylet plug in the assemble position. Other suitable types of needles can be used. Optionally, the needle may comprise a cut away proximal needle portion, through which a small amount of blood "flashback" flows, following a venipuncture, giving a visual indication that the needle has entered the vein correctly.

In another embodiment the apparatus of the invention comprises a needle, syringe means having a hub, and a protecting cover for the needle comprising an intravenous catheter tube, a manually guidable deformable elastomeric bore-defining tubular inserter integral with and in axial alignment with the catheter tube, the inserter optionally comprising syringe hub engageable tubular means extending from the inserter proximal end, the needle being mounted on the syringe hub to lie concentric with the catheter tube and inserter and extending through the bore of the inserter to beyond the distal end of the catheter tube, the inserter comprising opposed laterally extending wings adapted to be manually compressed together from an at-rest position to a needle control position, the bore of the inserter being sufficiently large to permit retraction of the needle from the catheter tube and the inserter when the inserter is at rest, and when the inserter wings are compressed to the needle control position being sufficiently constricted to enable the inserter to grip the needle firmly to permit inserter-forced injection of the distal end of the needle into the body of a patient.

In still another embodiment the apparatus of the invention comprises a hollow needle and a protecting cover for the needle comprising an intravenous catheter tube, a manually guidable deformable elastomeric bore-defining tubular inserter integral with and in axial alignment with the catheter tube, the inserter comprising a trailing tubular member with a proximal end closed by self-sealing diaphragm means, the trailing tubular member having side arm means adapted for transport of fluid through said trailing tubular member, the needle having a side opening and being adapted to be placed in piercing relation through the diaphragm means within the protecting cover with the side opening in communication with the side arm means for controlled transport of fluid through the needle and side arm means, the inserter comprising opposed laterally extending wings adapted to be manually compressed together from an at-rest position to a needle control position, the bore of the inserter being sufficiently large to permit retraction of the needle from the catheter tube and the inserter when the inserter is at rest, and when the inserter wings are compressed to the needle control position being sufficiently constricted to enable the inserter to grip the needle firmly to permit inserter-forced injection of the distal end of the needle into the body of a patient.

The inserter in the described embodiments is preferably of one-piece molded plastic construction; the inserter embodiment having a trailing tubular member with side arm means may suitably be in one piece or in two or more pieces joined together. The inserter is preferably made of flexibly deformable elastomer which is resilient, that is having a memory such that it can be deformed under manual pressure and yet can spontaneously regain its original shape in the at-rest position when such pressure is relieved. A suitable elastomer material, for example, is flexible polyvinyl chloride. The catheter tube is made of a suitable resilient synthetic resin such as polytetrafluoroethylene and the trailing tubular member is made in one or more parts of a suitable resilient synthetic resin such as flexible polyvinyl chloride. The catheter tube is secured unitarily to the inserter by any suitable means such as solvent bonding or adhesive bonding or by swaging or wedge locking. Also, the parts of the inserter where separate as with the trailing tubular member are secured together by similar means.

The body of the inserter encloses the circumference of the adjacent surface of the needle and is dimensioned in the at-rest position such that it readily accommodates axial displacement of the needle along the length of the catheter tube and inserter body. In other words, in the at-rest position the inserter body is sufficiently clear of the needle to avoid an interference fit. The inserter wings are deformable, serving when manually compressed together to deform the body of the inserter thereby reducing the included angle between the wings and constricting the lateral size of the axial opening of the inserter through which the needle passes, such that the body of the inserter tightly squeezes the adjacent outer needle surface for unitary manipulation of the inserter, needle and catheter. Thus, squeezing of the wings together unites the inserter, needle and catheter in controlled fashion, for unitary movement either proximal or distal to the site of injection. After making a venipuncture, as desired, the inserter may be utilized in the at-rest position to free up the needle and, while keeping the needle stationary, to axially displace the catheter further into the vein. With the catheter introduced into the vein, the squeezing force on the inserter wings is released, and the needle is slideably retracted relative to the catheter tube. At any convenient time subsequent to the venipuncture, the catheter tube may be pulled from the site by pulling the inserter.

These and other objects, features, and advantages of the present invention will become more fully apparent from the following description and appended claims taken in conjunction with the accompanying drawings wherein:

FIG. 1 is a perspective view of one preferred catheter apparatus of the invention shown in assembled relation with the needle tip exposed;

FIGS. 2, 3 and 3a are similar views of related embodiments;

FIG. 4 is a cross-section view taken on line 4—4 of FIG. 1; and

FIG. 5 is a cross-sectional enlarged view taken on line 5—5 of FIG. 1.

As shown in FIG. 1 the catheter apparatus 10 comprises a hollow needle 20, a catheter tube 30, inserter 40, and a trailing tubular member 50 which preferably may be a length of clear tubing. The needle 20 at its point end or distal end 21 is preferably bevelled. The needle suitably has a uniform bore or lumen 22 and extends through the catheter tube 30 and inserter 40. As shown in cross-section (FIG. 5) the body 41 is in the at-rest position wherein the needle 20 is separated from the tubular member 50 by an annular space 43. In the embodiments illustrated in FIGS. 1 and 2, the proximal end 23 of the needle is located within the tubular member 50 as shown in FIG. 4. A flexible filament or wire 24 is fixed to the proximal end 23 of the needle by any suitable means such as crimping, welding, adhesive or the like. The wire extends coaxially through the tubular member 50 and integrally joins with a needle control plug or male plug 25. The catheter tube 30 preferably has a tapered distal end 31. The tube 30 at its proximal end 32 is integrally joined with the body 41 of the inserter by any suitable means such as adhesive or solvent bonding or the like. In one preferred embodiment as shown in FIG. 4, the proximal end 32 comprises a preformed hollow conical collar 33 adapted at its distal end 34 to receive the catheter tube telescopically and at its proximal end 35 being flared out to accommodate, in the proximal to distal direction, threading of the needle through the catheter tube. The tubular member 50, at its distal end 51 and proximal end 52, integrally joins the inserter 40 and a hollow base member 53, respectively, by suitable means such as adhesive or solvent bonding or the like. The embodiment shown in FIG. 2 is similar to that shown in FIG. 1 except that the tubular member 50 is integrally joined with a Y-adaptor 60 (instead of a female plug) which provides branching through arms 60a and 60b. The branch via arm 60a includes extension tube 61, self-sealing plug 62 and control plug 25. The branch via arm 60b includes extension tube 63 and closure cap 64.

In the embodiment illustrated in FIG. 3, the needle 20 extends through the catheter tube 30, the inserter 40, and tubular member 50, in that order, and is secured to a hollow base member 53 which is adapted to sealingly engage the hub 71 of a hollow syringe hub extension 72, the latter being removably secured to the hub 73 of a syringe 70.

In the embodiment illustrated in FIG. 3a, a hollow needle 20 is carried on a hollow base member 53 which is suitably adapted to receive a syringe hub (not shown) or a plug or closure 54. Except for the distal end 21 and proximal end 23, the needle is covered in turn by a catheter tube 30, inserter 40 and Y-branch 60a of a trailing tubular member 50, the latter at its open proximal end 52 being sealed by a needle-pierceable self-sealing plug or diaphragm 55. The tubular member 50 has a branch 60b adjacent a flow slot 26 (not shown) located as represented in the needle in open communication with an extension tube 63 which is sealed by a closure cap 64.

For venipuncture using the catheter apparatus of the invention with the exposed needle tip as shown, the inserter wings 42a and 42b are squeezed together to the needle control position illustrated in broken outline in FIG. 5, and venipunction is made at the selected site. In the needle control position, as will be understood, the body 41 of the inserter is deformed or constricted into gripping relation with the needle for joint manipulation of the inserter, catheter and needle such that the desired intravenous placement of the needle point 21 is accomplished. The wings are then released to the at-rest position and, optionally after administration of fluid by syringe means, the needle is then withdrawn from the apparatus by retraction of the needle control plug 25 (FIG. 1 or FIG. 2) or the syringe 70 and syringe extension 72 (FIG. 3) or the hollow base member 53 (FIG. 3a). Advantageously, the position of the catheter tube 30 within the vein can be changed as desired by further axial manipulation of the inserter. Thus, the distal end 31 of the catheter tube can be advanced or retracted as required. Venous infusion of liquid can be accomplished, as desired, from a suitable liquid supply through tube means by way of the hollow base member 53 (FIGS. 1 and 3) or through tube 63 (FIG. 2) and flow slot 26 (FIG. 3a).

While the invention in catheter apparatus has been described in considerable detail, it will be realized by those skilled in the art that wide variation in such detail can be made without departing from the spirit of the invention as hereinafter claimed.

I claim:

1. An intravenous catheter apparatus comprising an intravenous catheter tube, a manually guidable circumferentially deformable elastomeric bore-defining tubular inserter integral with, and in axial alignment with, the catheter tube for use with a patient, and a needle concentric within the catheter tube and inserter and extending through at least part of the bore of the inserter to beyond the distal end of the catheter tube, the bore of the inserter being in open communication with the catheter tube lumen, the catheter tube and inserter being unitarily joined and adapted to be advanced or retracted as a unit axially in sliding relation along the needle, the inserter comprising opposed laterally extending wings adapted to be manually compressed together from an at-rest position to a needle control position, the bore of the inserter being sufficiently large to permit retraction of the needle from the catheter tube and the inserter when the inserter is at rest, and when the inserter wings are compressed to the needle control position being sufficiently constricted to enable the inserter to grip the needle firmly to permit inserter-forced injection of the distal end of the needle into the body of a patient.

2. In a stylet catheter, an internal stylet needle for making a venipuncture, a catheter tube telescopically surrounding the stylet and a manually guidable circumferentially deformable elastomeric bore-defining tubular inserter rigidly integral with the catheter tube, the bore of the inserter being in open communication with the catheter tube lumen, the catheter tube and inserter being unitarily joined and adapted to be advanced or retracted as a unit axially in sliding relation along the needle, the inserter generally loosely circumscribing, in the at-rest condition, a portion of the needle and having movable inserter wings so as to selectively accommodate (a) linear displacement of the inserter and the catheter tube axially along the needle when said inserter is in the at-rest condition and (b) joint displacement of the inserter, the catheter tube, and the needle when the wings are forcibly pressed together to close upon the needle.

3. In a catheter assembly,
a hollow needle for making a body puncture,
a catheter tube telescopically surrounding a distal portion of the needle,
and a hollow tubular inserter integral with and in open communication with the proximal open end of the catheter tube and telescopically surrounding a proximal portion of the needle, the catheter tube and inserter being unitarily joined in axial alignment and adapted to be advanced or retracted as a unit axially in sliding relation along the needle, the inserter comprising an elastic tubular body which is reversibly deformable to and from (a) an at-rest open position in slideable relation with the needle and (b) a laterally constricted position upon the needle, which inserter has opposed wings adapted to be gripped from manipulating the inserter and catheter assembly, the wings being squeezable together to cause the inserter body to be deformed to the laterally constricted position upon the needle such that the inserter is prevented from sliding on the needle.

4. A catheter as defined in claim 3 including a trailing tubular member integral with the proximal end of the inserter telescopically circumscribing a portion of the needle, the tubular member terminating in closure means.

5. A catheter as defined in claim 3 including a trailing length of clear tubing integral with the proximal end of the inserter telescopically circumscribing a portion of the needle, the clear tubing terminating in closure means comprising a socket adapted to receive a stylet plug.

6. A catheter as defined in claim 4 wherein the closure means comprises a socket adapted to receive a stylet plug such that flashback during a vascular puncture flows through the needle to the clear tubing where it is readily visible.

7. A catheter as defined in claim 4 wherein the closure means comprises leak proof plug means adapted for withdrawal of a stylet needle therethrough.

8. A catheter as defined in claim 4 wherein the closure means comprises leak proof means for infusing liquid into the clear tubing.

9. A catheter as defined in claim 4 wherein the closure means comprises syringe means for infusing liquid into the clear tubing.

10. A catheter as defined in claim 4 wherein the closure means comprises a Y-branch in communication with infusion means.

11. An intravenous catheter apparatus comprising a needle, syringe means having a hub, and a cover for the needle, the cover comprising an intravenous catheter tube and a manually guidable deformable elastomeric bore-defining tubular inserter integral with and in axial alignment with the catheter tube, the bore of the inserter being in open communication with the catheter tube lumen, the needle being mounted on the syringe hub to lie concentric within the catheter tube and inserter and extending through the bore of the inserter to beyond the distal end of the catheter tube, the inserter comprising opposed laterally extending wings adapted to be manually compressed together from at-rest position to a needle control position, the bore of the inserter being sufficiently large to permit retraction of the needle from the catheter tube and the inserter when the inserter is at rest, and when the inserter wings are compressed to the needle control position being sufficiently constricted to enable the inserter to grip the needle firmly to permit inserter-forced injection of the distal end of the needle into the body of a patient.

12. An intravenous catheter apparatus as defined in claim 11 wherein the cover comprises the catheter tube, the inserter and a trailing length of clear tubing.

13. An intravenous catheter apparatus comprising a hollow needle and a protecting cover for the needle comprising an intravenous catheter tube, a manually guidable deformable elastomeric bore-defining tubular inserter integral with and in axial alignment with the catheter tube, the bore of the inserter being in open communication with the catheter tube lumen, the inserter comprising a trailing tubular member with a proximal end closed by self-sealing diaphragm means, the trailing tubular member having a side arm means adapted for transport of fluid through said trailing tubular member, the needle having a side opening and being adapted to be placed in piercing relation through the diaphragm means within the protecting cover with the side opening in communication with the side arm means for transport of fluid through the needle and side arm means, the inserter comprising opposed laterally extending wings adapted to be manually compressed together from an at-rest position to a needle control position, the bore of the inserter being sufficiently large to permit retraction of the needle from the catheter tube and the inserter when the inserter is at rest, and when the inserter wings are compressed to the needle control position being sufficiently constricted to enable the inserter to grip the needle firmly to permit inserter-forced injection of the distal end of the needle into the body of a patient.

* * * * *